Figure 1:
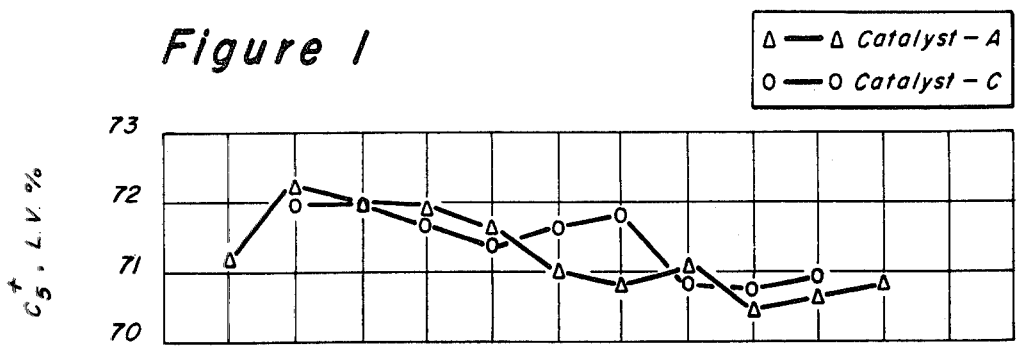

United States Patent [19]

Antos

[11] 4,358,399

[45] * Nov. 9, 1982

[54] ACTIVATED MULTIMETALLIC CATALYTIC COMPOSITE

[75] Inventor: George J. Antos, Bartlett, Ill.

[73] Assignee: UOP Inc., Des Plaines, Ill.

[ * ] Notice: The portion of the term of this patent subsequent to Nov. 20, 1996, has been disclaimed.

[21] Appl. No.: 246,828

[22] Filed: Mar. 23, 1981

Related U.S. Application Data

[60] Division of Ser. No. 82,436, Oct. 5, 1979, Pat. No. 4,268,377, which is a continuation-in-part of Ser. No. 848,699, Nov. 4, 1977, Pat. No. 4,183,804.

[51] Int. Cl.$^3$ .................. B01J 27/08; B01J 27/10; B01J 23/46
[52] U.S. Cl. .................. 252/441; 252/472; 252/466 PT
[58] Field of Search ................ 252/441, 442, 466 PT, 252/472

[56] References Cited

U.S. PATENT DOCUMENTS 3,789,020  1/1974  Carter et al. .................. 252/442
4,175,056  11/1979  Antos .................. 252/441

*Primary Examiner*—Patrick Garvin
*Attorney, Agent, or Firm*—James R. Hoatson, Jr.; Louis A. Morris; William H. Page, II

[57] ABSTRACT

A novel activated multimetallic catalytic composite especially useful for converting hydrocarbons comprises a combination of a catalytically effective amount of a pyrolyzed ruthenium carbonyl component with a porous carrier material containing a uniform dispersion of a catalytically effective amount of a platinum group component, which is maintained in the elemental metallic state during the incorporation and pyrolysis of the ruthenium carbonyl component, and of a rhenium component. In a highly preferred embodiment, this novel catalytic composite also contains a catalytically effective amount of a halogen component. The platinum group component, pyrolyzed ruthenium carbonyl component, rhenium component and optional halogen component are preferably present in the multimetallic catalytic composite in amounts, calculated on an elemental basis, corresponding to about 0.01 to about 2 wt. % of the uniformly dispersed platinum group metal, about 0.01 to about 2 wt. % of carbonyl-derived ruthenium, about 0.01 to about 5 wt. % rhenium and about 0.1 to about 3.5 wt. % of halogen. A key feature associated with the preparation of the subject catalytic composite is reaction of a ruthenium carbonyl complex with a porous carrier material containing a uniform dispersion of a rhenium component and of a platinum group component maintained in the elemental state, whereby the interaction of the ruthenium moiety with the platinum group moiety is maximized due to the platinophilic (i.e. platinum-seeking) propensities of the carbon monoxide ligand used in the ruthenium reagent.

16 Claims, 3 Drawing Figures

ACTIVATED MULTIMETALLIC CATALYTIC COMPOSITE

CROSS-REFERENCES TO RELATED DISCLOSURES

This application is a division of my prior, copending application Ser. No. 82,436 filed Oct. 5, 1979 and issued as U.S. Pat. No. 4,268,377 on May 19, 1981, which in turn is a continuation-in-part of my prior application Ser. No. 848,699 filed Nov. 4, 1977, and issued Jan. 15, 1980 as U.S. Pat. No. 4,183,804. All of the teachings of these prior applications are specifically incorporated herein by reference.

The subject of the present invention is a novel activated multimetallic catalytic composite which has remarkably superior activity, selectivity and resistance to deactivation when employed in a hydrocarbon conversion process that requires a catalytic agent having both a hydrogenation-dehydrogenation function and a carbonium ion-forming function. The present invention, more precisely, involves a novel dual-function activated and attenuated multimetallic catalytic composite which quite surprisingly enables substantial improvements in hydrocarbon conversion processes that have traditionally used a platinum group metal-containing, dual function catalyst. According to another aspect, the present invention comprehends the improved processes that are produced by the use of the instant activated platinum-ruthenium-rhenium catalyst system which is characterized by a unique reaction between a ruthenium carbonyl complex and a porous carrier material containing a uniform dispersion of a rhenium component and of a platinum group component maintained in the elemental metallic state, whereby the interaction between the ruthenium moiety and the platinum group moiety is maximized on an atomic level. In a specific aspect, the present invention concerns a catalytic reforming process which utilizes the subject catalyst to markedly improve activity, selectivity and stability characteristics associated therewith to a degree not heretofore realized for platinum-ruthenium or platinum-ruthenium-rhenium catalyst systems. Specific advantages associated with use of the present activated platinum-ruthenium-rhenium system in a catalytic reforming process relative to those observed with the conventionally prepared (i.e. by impregnation, coprecipitation and/or ion-exchange) prior art platinum-ruthenium or platinum-rhenium catalyst systems, are: (1) Increased ability to make octane at low severity operating conditions; (2) Augmented capability to maximize $C_5+$ reformate and hydrogen production by operating at severity levels at which the prior art system has not been successfully employed; (3) Enhanced ability to substantially expand the catalyst life before regeneration becomes necessary in conventional temperature-limited catalytic reforming units; (4) Vastly increased tolerance to conditions which are known to increase the rate of production of deactivating coke deposits; (5) Significantly diminished requirements for amount of catalyst to achieve same results as the prior art catalyst system at no sacrifice in catalyst life before regeneration; and (6) Capability of operating at significantly increased charge rates with the same amount of catalyst and at similar conditions as the prior art catalyst system without any sacrifice in catalyst life before regeneration.

Composites having a hydrogenation-dehydrogenation function and a carbonium ion-forming function are widely used today as catalysts in many industries, such as the petroleum and petrochemical industry, to accelerate a wide spectrum of hydrocarbon conversion reactions. Generally, the carbonium ion-forming function is thought to be associated with an acid-acting material of the porous, adsorptive, refractory oxide type which is typically utilized as the support or carrier for a heavy metal component such as the metals or compounds of metals of Groups V through VIII of the Periodic Table to which are generally attributed the hydrogenation-dehydrogenation function.

These catalytic composites are used to accelerate a wide variety of hydrocarbon conversion reactions such as hydrocracking, hydrogenolysis, isomerization, dehydrogenation, hydrogenation, desulfurization, cyclization, polymerization, alkylation, cracking, hydroisomerization, dealkylation, transalkylation, etc. In many cases, the commercial applications of these catalysts are in processes where more than one of the reactions are proceeding simultaneously. An example of this type of process is reforming wherein a hydrocarbon feedstream containing paraffins and naphthenes is subjected to conditions which promote dehydrogenation of naphthenes to aromatics, dehydrocyclization of paraffins to aromatics, isomerization of paraffins and naphthenes, hydrocracking and hydrogenolysis of naphthenes and paraffins, and the like reactions, to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffin compounds is contacted with a dual-function catalyst to produce an output stream rich in isoparaffin compounds.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) activity is a measure of the catalyst's ability to convert hydrocarbon reactants into products at a specified severity level where severity level means the conditions used—that is, the temperature, pressure, contact time, and presence of diluents such as $H_2$; (2) selectivity refers to the amount of desired product or products obtained relative to the amount of reactants charged or converted; (3) stability refers to the rate of change with time of the activity and selectivity parameters—obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield, relative to the amount of the charge, that is obtained at the particular activity or severity level; and stability is typically equated to the rate of change with time of activity, as measured by octane number of $C_{5+}$ product and of selectivity as measured by $C_{5+}$ yield. Actually the last statement is not strictly correct because generally a continuous reforming process is run to produce a constant octane $C_{5+}$ product with severity level being continuously adjusted to attain this result; and furthermore, the severity level is for this process usually varied by adjusting the conversion temperature in the reaction so that, in point of fact, the rate of change of activity finds response in the rate of change of conversion temperatures and changes in this last parameter are customarily taken as indicative of activity stability.

As is well known to those skilled in the art, the principal cause of observed deactivation or instability of a dual-function catalyst when it is used in a hydrocarbon conversion reaction is associated with the fact that coke forms on the surface of the catalyst during the course of the reaction. More specifically, in these hydrocarbon conversion processes the conditions utilized typically result in the formation of heavy, high molecular weight, black, solid or semi-solid, carbonaceous material which is a hydrogen-deficient polymeric substance having properties akin to both polynuclear aromatics and graphite. This material coats the surface of the catalyst and thus reduces its activity by shielding its active sites from the reactants. In other words, the performance of this dual-function catalyst is sensitive to the presence of carbonaceous deposits or coke on the surface of the catalyst. Accordingly, the major problem facing workers in this area of the art is the development of more active and/or selective catalytic composites that are not as sensitive to the presence of these carbonaceous materials and/or have the capability to suppress the rate of the formation of these carbonaceous materials on the catalyst. Viewed in terms of performance parameters, the problem is to develop a dual-function catalyst having superior activity, selectivity, and stability characteristics. In particular, for a reforming process the problem is typically expressed in terms of shifting and stabilizing the $C_{5+}$ yield-octane relationship at the lowest possible severity level—$C_{5+}$ yield being representative of selectivity and octane being proportional to activity.

I have now found a dual-function activated and multimetallic catalytic composite which possesses improved activity, selectivity and stability characteristics relative to similar catalysts of the prior art when it is employed in a process for the conversion of hydrocarbons of the type which have heretofore utilized dual-function, platinum group metal-containing catalytic composites such as processes for isomerization, hydroisomerization, dehydrogenation, desulfurization, denitrogenization, hydrogenation, alkylation, dealkylation, disproportionation, polymerization, hydrodealkylation, transalkylation, cyclization, dehydrocyclization, cracking, hydrocracking, halogenation, reforming and the like processes. In particular, I have now established that an activated multimetallic catalytic composite, comprising a combination of a catalytically effective amount of a pyrolyzed ruthenium carbonyl component with a porous carrier material containing catalytically effective amounts of a platinum group component and of a rhenium component, can enable the performance of hydrocarbon conversion processes utilizing dual-function catalysts to be substantially improved if the platinum group component is relatively uniformly dispersed throughout the porous carrier material prior to contact with the ruthenium carbonyl reagent; if the oxidation state of the platinum group component is maintained in the elemental metallic state prior to, during contact with the ruthenium carbonyl reagent and during the subsequent pyrolysis thereof; and if high temperature treatment in the presence of oxygen and/or water of the resulting reaction product is avoided. A specific example of my discovery involves my finding that an activated acidic multimetallic catalytic composite, comprising a combination of a catalytically effective amount of a pyrolyzed ruthenium carbonyl component with a porous carrier material containing a uniform dispersion of catalytically effective amounts of a platinum group component, which is maintained in the elemental metallic state during the incorporation and pyrolysis of the ruthenium carbonyl component, of a rhenium component and of a halogen component, can be utilized to substantially improve the performance of a hydrocarbon reforming process which operates on a low octane gasoline fraction to produce a high octane reformate or aromatic-rich reformate. In the case of a reforming process, some of the major advantages associated with the use of the novel multimetallic catalytic composite of the present invention include: (1) acquisition of the capability to operate in a stable manner in a high severity operation; for example, a low or moderate pressure reforming process designed to produce a $C_{5+}$ reformate having an octane of at least about 100 F-1 clear; (2) substantially increased activity for octane upgrading reactions relative to the performance of prior art bimetallic platinum-ruthenium or platinum-rhenium catalyst systems (i.e. prepared by conventional procedures such as impregnation, coprecipitation or ion-exchange); (3) increased capability to operate for extended periods of time in high severity, temperature-limited existing catalytic reforming units and (4) substantially augmented capacity to maximize $C_{5+}$ yield and hydrogen production. In sum the present invention involves the remarkable finding that the addition of a pyrolyzed ruthenium carbonyl component to a porous carrier material containing a uniform dispersion of a catalytically effective amount of a platinum group component maintained in the elemental metallic state and of a rhenium component, can enable the performance characteristics of the resulting activated multimetallic catalytic composite to be sharply and materially improved relative to those associated with the prior art platinum-ruthenium or platinum-rhenium catalyst systems.

It is, accordingly, an object of the present invention to provide an activated multimetallic hydrocarbon conversion catalyst having vastly superior performance characteristics relative to the prior art platinum-ruthenium catalyst system when utilized in a hydrocarbon conversion process. A second object is to provide an activated multimetallic acidic catalyst having dual-function hydrocarbon conversion performance characteristics which are relatively insensitive to the deposition of coke-forming, hydrocarbonaceous materials thereon and to the presence of sulfur contaminants in the reaction environment. A third object is to provide perferred methods of perparation of this activated and attenuated multimetallic catalytic composite which methods insure the achievement and amintenace of its unique properties. Another object is to provide a novel platinum-ruthenium-rhenium catalyst system superior activity, selectivity and stability characteristics relative to the platinum-ruthenium and platinum-rhenium catalyst systems of the prior art. Another object is to provide a novel acidic multimetallic hydrocarbon conversion catalyst which utilizes a pyrolyzed ruthenium carbonyl component to beneficially interact with and selectively promote an acidic catalyst containing a halogen component and a uniform dispersion of a platinum group component maintained in the metallic state and of a rhenium component.

Without the intention of being limited by the following explanation, I believe my discovery that ruthenium carbonyl can, quite unexpectedly, be used under the circumstances described herein to synthesize an entirely new type of platinum-ruthenium-rhenium catalyst system, is attributable to one or more unusual and unique routes to greater platinum-ruthenium interaction that are opened or made available by the novel chemistry associated with the reaction of a ruthenium carbonyl reactant with a supported, uniformly dispersed platinum group metal. Before considering in detail each of these possible routes to greater platinum-ruthenium interaction it is important to understand that: (1) The word "platinum" is used in this explanation to mean any one of the platinum group metals except ruthenium; (2) The unexpected results achieved with my catalyst systems are measured relative to conventional platinum-ruthenium or platinum-rhenium catalyst systems prepared by coimpregnation of platinum or of platinum and rhenium; (3) The expression "ruthenium moiety" is intended to mean the catalytically active form of the ruthenium entity (derived from the ruthenium carbonyl) in the catalyst system: (4) Metallic carbonyls have been suggested generally in the prior art for use in making catalysts such as in U.S. Pat. Nos. 3,591,649; 4,048,110 and 2,798,051, but no one to my knowledge has ever suggested using these reagents in the platinum-ruthenium or platinum-ruthenium-rhenium catalyst systems, particularly where substantially all of the platinum group component of the catalyst is present in a reduced form (i.e. the metal) prior to incorporation of the ruthenium carbonyl component; (5) Ruthenium sites derived from the carbonyl are to be distinguished from ruthenium sites that are established in the composite by conventional preparatory methods when the uniformly dispersed platinum group metal happens to be ruthenium. One route to greater platinum-ruthenium interaction enabled by the present invention comes from the theory that the effect of ruthenium on a platinum catalyst is very sensitive to the particle size of the ruthenium moiety; since in my procedure the ruthenium moiety is put on the catalyst in a form where it is complexed with a carbon monoxide molecule which is known to have a strong affinity for platinum, it is reasonable to assume that when the platinum is widely dispersed on the support, one effect of the CO ligand is to pull the ruthenium moiety towards the platinum sites on the catalyst, thereby achieving a dispersion and particle size of the ruthenium moiety in the catalyst which closely imitates the corresponding platinum conditions (i.e. this might be called a piggy-back theory). The second route to greater platinum-ruthenium interaction is similar to the first and depends on the theory that the effect of ruthenium on a platinum catalyst is at a maximum when the ruthenium moiety is attached to individual platinum sites; the use of platinophilic CO ligands, as called for by the present invention, then acts to facilitate adsorption or chemisorption of the ruthenium moiety on the platinum site so that a substantial portion of the ruthenium moiety is deposited or fixed on or near the platinum site where the platinum acts to anchor the ruthenium, thereby making it more resistant to sintering at high temperature. The third route to greater platinum-ruthenium interaction is based on the theory that the active state for the ruthenium moiety in the ideal platinum-ruthenium catalyst system is the elemental metallic state and that the best platinum-ruthenium interaction is achieved when the proportion of the ruthenium in the metallic state is maximized; using a ruthenium carbonyl compound to introduce the ruthenium into the catalytic composite conveniently ensures availability of more ruthenium metal because all of the ruthenium in this reagent is present in the elemental metallic state. Another route to greater platinum-ruthenium interaction is derived from the theory that oxygen at high temperature is detrimental to both the active form of the ruthenium moiety (i.e. the metal) and the dispersion of same on the support (i.e. oxygen at high temperatures is suspected of causing sintering of the ruthenium moiety); since the catalyst of the present invention is not subject to high temperature treatment with oxygen after the ruthenium moiety is incorporated, maximum platinum-ruthenium interaction is obviously preserved. The final theory for explaining the greater platinum-ruthenium interaction associated with the instant catalyst relates to the idea that the active sites for the platinum-ruthenium catalyst are basically platinum metal crystallites that have had their surface enriched in ruthenium metal; since the concept of the present invention requires the ruthenium to be laid down on the surface of well-dispersed platinum crystallites via a platinophilic ruthenium carbonyl complex, the probability of surface enrichment is greatly increased for the present procedure relative to that associated with the random, independent dispersion of both crystallites that has characterized the prior art preparation procedures. It is of course to be recognized that all of these factors may be involved to some degree in the overall explanation of the impressive results associated with my activated and attenuated catalyst system. A further fact to be kept in mind is that the conventional platinum-ruthenium catalyst system has never been noted for a significant activity improvement; in contrast, my activated platinum-ruthenium catalyst system (as is demonstrated in my prior application Ser. No. 848,699) gives much better activity than the conventional platinum-ruthenium catalyst system and, even more surprising, this activity advantage is coupled with dramatic increases in $C_5+$ yield selectivity, hydrogen production, activity-stability and selectivity-stability.

In the special case where the uniformly dispersed platinum group component of the instant catalyst system is ruthenium, my explanation of the surprising ruthenium-ruthenium interaction enabled by the present invention is based on my belief that the type of catalytic site established in the composite by conventional incorporation procedures is vastly different than the catalytic site derived from ruthenium carbonyl interaction. The principal evidence for this distrinction essentially involves the fact that I have never observed conventional ruthenium sites to beneficially interact with a uniformly dispersed platinum metal in such a manner as to promote and stabilize the resulting catalyst. Consequently, it is my opinion that ruthenium derived from a carbonyl gives a fundamentally different catalytic effect (when it is established in a porous carrier material pursuant to my invention) than ruthenium derived from conventional sources; for example—chlororuthenic acid or ruthenium trichloride.

Against this background then, the present invention is, in one embodiment, a novel trimetallic catalytic composite comprisng a combination of a catalytically effective amount of a pyrolyzed ruthenium carbonyl component with a porous material containing a uniform dispersion of catalytically effective amounts of a platinum group component, which is maintained in the elemental metallic state during the incorporation and pyrolysis of the ruthenium carbonyl component, and of a rhenium component.

In another embodiment, the subject catalytic composite comprises a combination of a catalytically effective amount of a pyrolyzed ruthenium carbonyl component with a porous carrier material containing a catalytically effective amount of a halogen component and a uniform dispersion of catalytically effective amounts of a platinum group component, which is maintainedin the elemental metallic state during the incorporation and pyrolysis of the ruthenium carbonyl component, and of a rhenium component.

In yet another embodiment the present invention involves a combination of a pyrolyzed ruthenium carbonyl component with a porous carrier material containing a halogen component and a uniform dispersion of a platinum group component, which is maintained in the elemental metallic state during the incorporation and pyrolysis of the ruthenium carbonyl component, and of a rhenium component, wherein these components are present in amounts sufficient to result in the composite containing, calculated on an elemental basis, about 0.01 to about 2 wt. % platinum group meta, about 0.01 to about 2 wt. % ruthenium metal (derived from the carbonyl), about 0.01 to about 5 wt. % rhenium and about 0.1 to about 3.5 wt. % halogen.

In still another embodiment, the present invention comprises any of the catalytic composites defined in the previous embodiments wherein the porous carrier material contains, prior to the addition of the pyrolyzed ruthenium carbonyl component, not only platinum group and rhenium components but also a catalytically effective amount of a component selected from the group consisting of zinc, tin, lead, germanium, cobalt, nickel, iron, tungsten, chromium, molybdenum, bismuth, indium, gallium, cadmium, tantalum, uranium, copper, silver, gold, one or more of the rare earth metals and mixtures thereof.

In another aspect, the invention is defined as a catalytic composite comprising the pyrolyzed reaction product formed by reacting a catalytically effective amount of a ruthenium carbonyl compound or complex with a porous carrier material containing a uniform dispersion of catalytically effective amounts of a platinum group component, which is maintained in the elemental metallic state during the incorporation and pyrolysis of the ruthenium carbonyl component, and of a rhenium component, and thereafter subjecting the resulting reaction product to pyrolysis conditions selected to decompose the ruthenium carbonyl component.

An ancillary embodiment of the present invention involves a method of preparing any of the catalytic composites defined in the previous embodiments, the method comprising the steps of: (a) reacting a ruthenium carbonyl complex with a porous carrier material containing a uniform dispersion of the platinum group component maintained in the elemental metallic state and of the rhenium component, and thereafter, (b) subjecting the resulting reaction product to pyrolysis conditions selected to decompose the ruthenium carbonyl component, without oxidizing either the platinum group or ruthenium components.

A further embodiment involves a process for the conversion of hydrocarbon which comprises contacting the hydrocarbon and hydrogen with the activated catalytic composite defined in any of the previous embodiments at hydrocarbon conversion conditions.

A highly preferred embodiment comprehends a process for reforming a gasoline fraction which comprises contacting the gasoline fraction and hydrogen with the activated multimetallic catalytic composites defined in any one of the prior embodiments at reforming conditions selected to produce a high octane reformate.

An especially preferred embodiment is a process for the production of aromatic hydrocarbons which comprises contacting a hydrocarbon fraction rich in aromatic precursors and hydrogen with an acidic catalytic composite comprising a combination of a catalytically effective amount of a pyrolyzed ruthenium carbonyl component with a porous carrier material containing catalytically effective amounts of a halogen component, a rhenium component, and a uniform dispersion of a catalytically effective amount of a platinum group component, which is maintained in the elemental metallic state during the incorporation and pyrolysis of the ruthenium carbonyl component. This contacting is performed at aromatic production conditions selected to produce an effluent stream rich in aromatic hydrocarbons.

Other objects and embodiments of the present invention relate to additional details regarding the essential and preferred catalytic ingredients, preferred amount of ingredients, appropriate methods of catalyst preparation, operating conditions for use with the novel catalyst in the various hydrocarbon conversion processes in which it has utility, and the like particulars, which are hereinafter given in the following detailed discussion of each of the essential and preferred features of the present invention.

Considering first the porous carrier material utilized in the present invention, it is preferred that the material be a porous, adsorptive, high surface area support having a surface area of about 25 to about 500 m$^2$/g. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically prepared and naturally occurring, which may or may not be acid treated for example, attapulgus clay, china clay, diatomaceous earth, fuller's earth, kaolin, kieselguhr, etc., (3) ceramics, porcelain, crushed firebrick, bauxite; (4) refractory inorganic oxides such as alumina, titanium dioxide, zirconium dioxide, chromium oxide, beryllium oxide, vanadium oxide, cesium oxide, hafnium oxide, zinc oxide, magnesia, boria, thoria, silica-alumina, silicamagnesia, chromia-alumina, alumina-boria, silica-zirconia, etc.; (5) crystalline zeolitic aluminosilicates such as naturally occurring or synthetically prepared mordenite and/or faujasite, either in the hydrogen form or in a form which has been treated with multivalent cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as gamma-, eta-, and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma- or eta-alumina. Preferred carrier materials have an apparent bulk density of about 0.3 to about 0.8 g/cc and surface area characteristics such that the average pore diameter is about 20 to 300 Angstroms, the pore volume is about 0.1 to about 1 cc/g and the surface area is about 100 to about 500 $m^2/g$. In general, best results are typically obtained with a gamma-alumina carrier material which is used in the form of spherical particles having: a relatively small diameter (i.e. typically about 1/16 inch), an apparent bulk density of about 0.3 to about 0.8 g/cc. a pore volume of about 0.4 ml/g and a surface area of about 150 to about 250 $m^2/g$.

The preferred alumina carrier material may be prepared in any suitable manner and may be synthetically prepared or natural occurring. Whatever type of alumina is employed, it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide, to a salt of alumina such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere, and alumina spheres may be continuously manufactured by the well known oil drop method which comprises: forming an alumina hydrosol by any of the techniques taught in the art and preferably by reacting aluminum metal with hydrochloric acid, combining the resultant hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

Another particularly preferred alumina carrier material is synthesized from a unique crystalline alumina powder which has been characterized in U.S. Pat. Nos. 3,852,190 and 4,012,313 as a byproduct from a Ziegler higher alcohol synthesis reaction as described in Zeigler's U.S. Pat. No. 2,892,858. For purposes of simplification, the name "Ziegler alumina" is used herein to identify this material. It is presently available from the Conoco Chemical Division of Continental Oil Company under the trademark Catapal. This material is an extremely high purity alpha-alumina monohydrate (boehmite) which after calcination at a high temperature has been shown to yield a high purity gamma-alumina. It is commercially available in three forms: (1) Catapal SB—a spray dried powder having a typical surface area of 250 $m^2/g$; (2) Catapal NG—a rotary kiln dried alumina having a typical surface area of 180 $m^2/g$; and (3) Dispal M—a finely devided dispersable product having a typical surface area of about 185 $m^2/g$. For purposes of the present invention, the preferred starting material is the spray dried powder, Catapal SB. This alpha-alumina monohydrate powder may be formed into a suitable catalyst material according to any of the techniques known to those skilled in the catalyst carrier material forming art. Spherical carrier material particles can be formed, for example, from this Ziegler alumina by: (1) converting the alpha-alumina monohydrate powder into an alumina sol by reaction with a suitable peptizing agent and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disc until spherical particles are formed which can then be dried and calcined to form the desired particles of spherical carrier material; and (3) wetting the powder with a suitable peptizing agent and thereafter rolling particles of the powder into spherical masses of the desired size in much the same way that children have been known to make parts of snowmen by rolling snowballs down hills covered with wet snow. This alumina powder can also be formed in any other desired shape or type of carrier material known to those skilled in the art such as rods, pills, pellets, tablets, granules, extrudates and the like forms by methods well known to the practitioners of the catalyst carrier material forming art. The preferred type of carrier material for the present invention is a cylindrical extrudate having a diameter of about 1/32" to about ⅛" (especially about 1/16") and a length to diameter (L/D) ratio of about 1:1 to about 5:1, with a L/D ratio of about 2:1 being especially preferred. The especially preferred extrudate form of the carrier material is preferably prepared by mixing the alumina powder with water and a suitable peptizing agent such as nitric acid, acetic acid, aluminum nitrate and the like material until an extrudable dough is formed. The amount of wter added to form the dough is typically sufficient to give a loss on ignition (LOI) at 500° C. of about 45 to 65 wt. %, with a value of about 55 wt. % being especially preferred. On the other hand, the acid addition rate is generally sufficient to provide about 2 to 7 wt. % of the volatile free alumina powder used in the mix, with a value of about 3 to 4% being especially preferred. The resulting dough is then extruded through a suitably sized die to form extrudate particles. These particles are then dried at a temperature of about 500° to 800° F. for a period of about 0.1 to about 5 hours and thereafter calcined at a temperature of about 900° F. to about 1500° F. for a period of about 0.5 to about 5 hours to form the preferred extrudate particles of the Ziegler alumina carrier material. In addition, in some embodiments of the present invention the Ziegler alumina carrier material may contain minor proportions of other well known refractory inorganic oxides such as silica, titanium dioxide, zirconium dioxide, chromium oxide, beryllium oxide, vanadium oxide, cesium oxide, hafnium oxide, zinc oxide, iron oxide, cobalt oxide, magnesia, boria, thoria, and the like materials which can be blended into the extrudable dough prior to the extrusion of same. In the same manner crystalline zeolitic aluminosilicates such as naturally occurring or synthetically prepared mordenite and/or faujasite, either in the hydrogen form or in a form which has been treated with a multivalent cation, such as a rare earth, can be incorporated into this carrier material by blending finely divided particles of same into the extrudable dough prior to extrusion of same. A preferred carrier material of this type is substantially pure Ziegler alumina having an apparent bulk density (ABD) of about 0.6 to 1 g/cc (especially an ABD of about 0.7 to about 0.85 g/cc), a surface area of about 150 to about 280 m$^2$/g (preferably about 185 to about 235 m$^2$/g), and a pore volume of about 0.3 to about 0.8 cc/g.

A first essential ingredient of the subject catalyst is the platinum group component. That is, it is intended to cover the use of platinum, iridium, osmium, ruthenium, rhodium, palladium, or mixtures thereof as a first component of the activated catalytic composite. It is an essential feature of the present invention that substantially all of this platinum group component is uniformly dispersed throughout the porous carrier material in the elemental metallic state prior to the incorporation of the ruthenium carbonyl ingredient. Generally, the amount of this component present in the form of catalytic compsites is small and typically will comprise about 0.01 to about 2 wt. % of final catalytic composite, calculated on an elemental basis. Excellent results are obtained when the catalyst contains about 0.05 to about 1 wt. % of platinum, iridium, rhodium or palladium or ruthenium metal. particularly preferred mixtures of these platinum group metals for use in the composite of the present invention are: (1) platinum and iridium, (2) platinum and rhodium and (3) platinum and ruthenium.

This platinum group component may be incorporated into the porous carrier material in any conventional manner known to result in a relatively uniform distribution of this component in the carrier material such as coprecipitation or cogelation, ion-exchange or impregnation. The preferred method of preparing the catalyst involves the utilization of a soluble, decomposable compound of platinum group metal to impregnate the carrier material in a relatively uniform manner. For example, this component may be added to the support by commingling the latter with an aqueous solution of chloroplatinic or chloroiridic or chlororuthenic or chloropalladic acid. Other water-soluble compounds or complexes of platinum group metals may be employed in impregnation solutions and include ammonium chloroplatinate, bromoplatinic acid, platinum trichloride, ruthenium trichloride, platinum tetrachloride hydrate, platinum dichlorocarbonyl dichloride, dinitrodiaminoplatinum, sodium tetranitroplatinate (II), palladium chloride, palladium nitrate, palladium sulfate, diamminepalladium (II) hydroxide, tetramminepalladium (II) chloride, hexamminerhodium chloride, rhodium carbonylchloride, rhodium trichloride hydrate, rhodium nitrate, sodium hexachlororhodate (III), sodium hexanitrorhodate (III) iridium tribromide, iridium dichloride, iridium tetrachloride, sodium hexanitroiridate (III), potassium or sodium chloroiridate, potassium rhodium oxalate, etc. The utilization of a platinum, iridium, rhodium, or palladium or ruthenium chloride compound, such as chloroplatinic, chloroiridic, or chloropalladic acid, or rhodium trichloride hydrate, or chlororuthenic acid is preferred since it facilitates the incorporation of both the platinum group component and at least a minor quantity of the preferred halogen component in a single step. Hydrogen chloride or the like acid is also genrally added to the impregnation solution in order to further facilitate the incorporation of the halogen component and the uniform distribution of the metallic component throughout the carrier material. In addition, it is generally preferred to impregnate the carrier material after it has been calcined in order to minimize the risk of washing away the valuable platinum group compound.

A second essential constituent of the multimetallic catalyst of the present invention is a rhenium component. This component may in general be present in the instant catalytic composite in any catalytically available form such as the elemental metal, a compound like the oxide, hydroxide, halide, oxyhalide, sulfide, or in chemical combination with one or more of the other ingredients of the catalyst. Although it is not intended to restrict the present invention by this explanation, it is believed that best results are obtained when the rhenium component is present in the composite in a form wherein substantially all of the rhenium moiety is in the elemental metallic state or in a state which is reducible to the elemental metallic state under hydrocarbon conversion conditions or in a mixture of these states. This rhenium component can be used in any amount which is catalytically effective, with good reslts obtained, on an elemental basis, with about 0.01 to about 5 wt. % rhenium in the catalyst. Best results are ordinarily achieved with about 0.05 to about 1 wt. % rhenium, calculated on an elemental basis and with an atomic ratio of rhenium to platinum group metal of about 0.1:1 to about 10:1, especially about 0.5:1 to about 5:1.

This rhenium component may be incorporated into the porous carrier material in any suitable manner known to the art to result in a relatively uniform dispersion of the rhenium moiety in the carrier material, such as by coprecipitation or cogellation or coextrusion with the porous carrier material, ion exchange with the gelled carrier material, or impregnation of the carrier material either after, before, or during the period when it is dried and calcined. It is to be noted that it is intended to include within the scope of the present invention all conventional methods for incorporating and simultaneously uniformly distributing a metallic component in a catalytic composite and the particular method of incorporation used is not deemed to be an essential feature of the present invention. One acceptable method of incorporating the rhenium component into the porous carrier material involves cogelling or coprecipitating the rhenium component in the form of the corresponding hydrous oxide during the preparation of the preferred carrier material, alumina. This method typically involves the addition of a suitable sol-soluble and decomposable rhenium compound such as perrhenic acid or a salt thereof to the alumina hydrosol and then combining the hydrosol with a suitable gelling agent and dropping the resulting mixture into an oil bath, etc., as explained in detail hereinbefore. After drying and calcining the resulting gelled carrier material in air, there is obtained an intimate combination of alumina and rhenium oxide and/or oxychloride. An especially preferred method of incorporating the rhenium component into the porous carrier material involves utilization of a souble, decomposable compound of rhenium to impregnate the porous carrier material. In general, the solvent used in this impregnation step is selected on the basis of the capability to dissolve the desired rhenium compound without adversely affecting the carrier material or the other ingredients of the catalyst—for example, a suitable alcohol, ether, acid and the like solvents. The solvent is preferably an aqueous, acidic solution. The rhenium component may be added to the carrier material by commingling the latter with an aqueous acidic solution of suitable rhenium salt, complex, or compound such as perrhenic acid, ammonium perrhenate, sodium perrhenate, potassium perrhenate, potassium rhenium oxychloride ($K_2ReOCl_5$), potassium hexachlororhenate (IV), rhenium chloride, rhenium heptoxide and the like compounds. A particularly preferred impregnation solution comprises an acidic aqueous solution of perrhenic acid. Suitable acids for use in the impregnation solution are: inorganic acids such as hydrochloric acid, nitric acid, and the like, and strongly acidic organic acids such as oxalic acid, malonic acid, citric acid, and the like. In general, the rhenium component can be impregnated either prior to, simultaneously with, or after the platinum group component is added to the carrier material. However, excellent results are obtained when the rhenium component is added simultaneously with the addition of the platinum group component.

It is especially preferred to incorporate a halogen component into the platinum group metal- and rhenium-containing porous carrier material prior to the reactions thereof with the ruthenium carbonyl reagent. Although the precise form of the chemistry of the association of the halogen component with this carrier material is not entirely known, it is customary in the art to refer to the halogen component as being combined with the carrier material, or with the platinum group and/or rhenium components in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the platinum group component. For example, the halogen may be added, at any stage of the preparation of the carrier material or to the calcined carrier material, as an aqueous solution of a suitable, decomposable halogen-containing compound such as hydrogen flouride, hydrogen chloride, hydrogen bromide, ammonium chloride, etc. The halogen component or a portion thereof, may be combined with the carrier material during the impregnation of the latter with the platinum group and/or rhenium components; for example, through the utilization of a mixture of chloroplatinic acid and hydrogen chloride. In another situation, the alumina hydrosol which is typically utilized to form a preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5%, by weight of halogen, calculated on an elemental basis. In isomerization or hydrocracking embodiments, it is generally preferred to utilize relatively larger amounts of halogen in the catalyst—typically, ranging up to about 10 wt. % halogen calculated on an elemental basis, and more preferably, about 1 to about 5 wt. %. It is to be understood that the specified level of halogen component in the instant activated and attenuated catalyst can be achieved or maintained during use in the conversion of hydrocarbons by continuously or periodically adding to the reaction zone a decomposable halogen-containing compound such as an organic chloride (e.g. ethylene dichloride, carbon tetrachloride, t-butyl chloride) in an amount of about 0.5 to 100 wt. ppm. of the hydrocarbon feed, and preferably about 1 to 10 wt. ppm.

After the platinum group and rhenium components are combined with the porous carrier material, the resulting platinum group metal- and rhenium containing carrier material will generally be dried at a temperature of about 200° F. to about 600° F. for a period of typically about 1 to about 24 hours or more and thereafter oxidized at a temperature of about 700° F. to about 1100° F. in an air or oxygen atmosphere for a period of about 0.5 to about 10 or more hours or converts substantially all of the platinum group and rhenium components to the corresponding metallic oxides. When the preferred halogen component is utilized in the present composition, best results are generally obtained when the halogen content of the platinum group metal- and rhenium-containing carrier material is adjusted during this oxidation step by including a halogen or a halogen-containing compound in the air or oxygen atmosphere utilized. For purposes of the present invention, the particularly preferred halogen is chlorine and it is highly recommended that the halogen compound utilized in this halogenation step be either hydrochloric acid or a hydrochloric acid producing substance. In particular, when the halogen component of the catalyst is chlorine, it is preferred to use a molar ratio of $H_2O$ to HCl of about 5:1 to about 100:1 during at least a portion of the oxidation step which follows the platinum group metal impregnation in order to adjust the final chlorine content of the catalyst to a range of about 0.1 to about 3.5 wt. %. Preferably, the duration of this halogenation step is about 1 to 5 or more hours.

A crucial feature of the present invention involves subjecting the resulting oxidized, platinum group metal- and rhenium-containing, and typically halogen-treated, carrier material to a substantially water-free reduction step before the incorporation of the ruthenium component by means of the ruthenium carbonyl reagent. The importance of this reduction step comes from my observation that when an attempt is made to prepare the instant catalytic composite without further reducing the platinum group component, no significant improvement in the platinum-ruthenium-rhenium catalyst system is obtained; but another way, it is my finding that it is essential for the platinum group component to be well dispersed in the porous carrier material in the elemental metallic state prior to incorporation of the ruthenium carbonyl component by the unique procedure of the present invention in order for synergistic interaction of the ruthenium carbonyl with the dispersed platinum group metal to occur according to the theories that I have previously explained. Accordingly, this reduction step is designed to reduce substantially all of the platinum group component to the elemental metallic state and to assure a relatively uniform and finely divided dispersion of this metallic component throughout the porous carrier material. Preferably a substantially pure and dry hydrogen stream (by the use of the word "dry" I mean that it contains less than 20 vol. ppm. water and preferably less than 5 vol. ppm. water) is used as the reducing agent in this step. The reducing agent is contacted with the oxidized, platinum group metal-and rhenium-containing carrier material at conditions including a reduction temperature of about 450° F. to about 1200° F. for a period of about 0.5 to about 10 or more hours selected to reduce substantially all of the platinum group component to the elemental metallic state. Once this condition of finely divided dispersed platinum group metal in the porous carrier material is achieved, it is important that environments and/or conditions that could disturb or change this condition be avoided; specifically, I much prefer to maintain the freshly reduced carrier material containing the platinum group metal under a blanket of inert gas to avoid any possibility of contamination of same either by water or by oxygen.

A third essential ingredient of the present activated and attenuated catalytic composite is a special ruthenium component which I have chosen to characterize as a pyrolyzed ruthenium carbonyl in order to emphasize that the ruthenium moiety of interest in my invention is the ruthenium produced by decomposing a ruthenium carbonyl in the presence of a finely divided dispersion of a platinum group metal and in the absence of materials such as oxygen or water which could interfere with the basic desired interaction of the ruthenium carbonyl component with the platinum group metal component as previously explained. In view of the fact that all of the ruthenium contained in a ruthenium carbonyl compound is present in the elemental metallic state, an essential requirement of my invention is that the resulting reaction product of the ruthenium carbonyl compound or complex with the platinum group metal-and rhenium-loaded carrier material is not subjected to conditions which could in any way interfere with the maintenance of the ruthenium moiety in the elemental metallic state; consequently, avoidance of any conditions which would tend to cause the oxidation of any portion of the ruthenium ingredient or of the platinum group ingredient is a requirement for full realization of the synergistic interaction enabled by the present invention. This ruthenium carbonyl component may be utilized in the resulting composite in any amount that is catalytically effective with the preferred amount typically corresponding to about 0.01 to about 2 wt. % thereof, calculated on an elemental ruthenium basis. Best results are ordinarily obtained with about 0.05 to about 1 wt. % ruthenium. Best results are also achieved when the amount of the ruthenium carbonyl component is set as a function of the amount of the platinum group component to achieve a carbonyl-derived ruthenium to platinum group metal atomic ratio of about 0.1:1 to about 5:1, with an especially useful range comprising about 0.2:1 to about 3:1 and with superior results achieved at an atomic ratio of ruthenium to platinum group metal of about 0.5:1 to about 1.0:1.

The ruthenium carbonyl ingredient may be reacted with the reduced platinum group metal-and ruthenium-containing porous carrier material in any suitable manner known to those skilled in the catalyst formulation art which results in relatively good contact between the ruthenium carbonyl complex and the platinum group component contained in the porous carrier material. One acceptable procedure for incorporating the ruthenium carbonyl component into the composite involves sublimating this complex under conditions which enable it to pass into the vapor phase without being decomposed and thereafter contacting the resulting ruthenium carbonyl sublimate with the platinum group metal-and rhenium-containing porous carrier material under conditions designed to achieve intimate contact of the carbonyl reagent with the platinum group metal dispersed on the carrier material. Typically, this procedure is performed under vaccum at a temperature of about 70° to about 250° F. for a period of time sufficient to react the desired amount of ruthenium carbonyl with the carrier material. In some cases an inert carrier gas such as nitrogen can be admixed with the ruthenium carbonyl sublimate in order to facilitate the intimate contacting of same with the metal-containing porous carrier material. A particularly preferred way of accomplishing this reaction step is an impregnation procedure wherein metal-containing porous carrier material is impregnated with a suitable solution containing the desired quantity of the ruthenium carbonyl complex. For purposes of the present invention, organic solutions are preferred, although any suitable solution may be utilized as long as it does not interact with the ruthenium carbonyl and cause decomposition of same. Obviously the organic solution should be anhydrous in order to avoid detrimental interaction of water with the ruthenium carbonyl complex. Suitable solvents are any of the commonly available organic solvents such as one of the available ethers, alcohols, ketones, aldehydes, paraffins, naphthenes and aromatic hydrocarbons, for example, acetone, acetyl acetone, benzaldehyde, pentane, hexane, carbon tetrachloride, methyl isopropyl ketone, benzene, n-butylether, diethyl ether, ethylene glycol, methyl isobutyl ketone, diisobutyl ketone and the like organic solvents. Best results are ordinarily obtained when the solvent is acetone; consequently, the preferred impregnation solution is ruthenium carbonyl dissolved in anhydrous acetone. The ruthenium carbonyl complex suitable for use in the present invention may be either the pure ruthenium carbonyl itself (i.e. $Ru(CO)_5$ or $Ru_3(CO)_{12}$) or a substituted ruthenium carbonyl halides including the ruthenium carbonyl halides including the chlorides, bromides, and iodides and the like substituted carbonyl complexes. After impregnation of the carrier material with the ruthenium carbonyl component, it is important that the solvent be removed or evaporated from the catalyst prior to decomposition of the ruthenium carbonyl component by means of the hereinafter described pyrolysis step. The reason for removal of the solvent is that I believe that the presence of organic materials such as hydrocarbons or derivatives of hydrocarbons during the pyrolysis step is highly detrimental to the synergistic interaction associated with the present invention. This solvent is removed by subjecting the ruthenium carbonyl impregnated carrier material to a temperature of about 100° F. to about 250° F. in the presence of an inert gas or under a vaccum condition until no further substantial amount of solvent is observed to come off the impregnated material. In the preferred case where acetone is used as the impregnation solvent, this drying of the impregnated carrier material typically takes about one half hour at a temperature of about 225° F. under moderate vacuum conditions.

After the ruthenium carbonyl component is incorporated into the platinum-and rhenium containing porous carrier material, the resulting composite is, pursuant to the present invention, subjected to pyrolysis conditions designed to decompose substantially all of the ruthenium carbonyl material, without oxidizing either the platinum group component or the decomposed ruthenium carbonyl component. This step is preferably conducted in an atmosphere which is substantially inert to the ruthenium carbonyl such as in a nitrogen or noble gas-containing atmosphere. Preferably this pyrolysis step takes place in the presence of a substantially pure and dry hydrogen stream. It is of course within the scope of the present invention to conduct the pyrolysis step under vacuum conditions. It is much preferred to conduct this step in the substantial absence of free oxygen and substances that could yield free oxygen under the conditions selected. Likewise it is clear that best results are obtained when this step is performed in the total absence of water and of hydrocarbons and other organic materials. I have obtained best results in pyrolyzing ruthenium carbonyl while using an anhydrous hydrogen stream at pyrolysis conditions including a temperature of about 300° F. to about 900° F. or more, preferably about 400° F. to about 750° F., a gas hourly space velocity of about 250 to about 1500 hr.$^{-1}$ for a period of about 0.5 to about 5 or more hours until no further evolution of carbon monoxide is noted. After the ruthenium carbonyl component has been pyrolyzed, it is a much preferred practice to maintain the resulting catalytic composite in an inert environment (i.e. a nitrogen or the like inert gas blanket) until the catalyst is loaded into a reaction zone for use in the conversion of hydrocarbons.

The resulting pyrolyzed catalytic composite may, in some cases, be beneficially subjected to a presulfiding step designed to incorporate in the catalytic composite from about 0.01 to about 1 wt. % sulfur calculated on an elemental basis. Preferably, this presulfiding treatment takes place in the presence of hydrogen and a suitable decomposable sulfur-containing compound such as hydrogen sulfide, lower molecular weight mercaptans, organic sulfides, etc. Typically, this procedure comprises treating the pyrolyzed catalyst with a sulfiding gas such as a mixture of hydrogen and hydrogen sulfide containing about 10 moles of hydrogen per mole of hydrogen sulfide at conditions sufficient to effect the desired incorporation of sulfur, generally including a temperature ranging from about 50° F. up to about 1000° F. It is generally a preferred practice to perform this presulfiding step under substantially water-free and oxygen-free conditions. It is within the scope of the present invention to maintain or achieve the sulfided state of the present catalyst during use in the conversion of hydrocarbons by continuously or periodically adding a decomposable sulfur-containing compound, selected from the above mentioned hereinbefore, to the reactor containing the activated and attenuated catalyst in an amount sufficient to provide about 1 to 500 wt. ppm., preferably about 1 to about 20 wt. ppm. of sulfur, based on hydrocarbon charge. According to another mode of operation, this sulfiding step may be accomplished during the pyrolysis step by utilizing a ruthenium carbonyl reagent which has a sulfur-containing ligand or by adding H$_2$S to the hydrogen stream which is preferably used therein.

In embodiments of the present invention wherein the instant activated multimetallic catalytic composite is used for the dehydrogenation of dehydrogenatable hydrocarbons or for the hydrogenation of hydrogenatable hydrocarbons, it is ordinarily a preferred practice to include an alkali or alkaline earth metal component in the composite before addition of the ruthenium carbonyl component and to minimize or eliminate the preferred halogen component. More precisely, this optional ingredient is selected from the group consisting of the compounds of the alkali metals—cesium, rubidium, potassium, sodium, and lithium—and the compounds of the alkaline earth metals—calcium, strontium, barium and magnesium. Generally, good results are obtained in these embodiments when this component constitutes about 0.1 to about 5 wt. % of the composite, calculated on an elemental basis. This optional alkali or alkaline earth metal component can be incorporated into the composite in any of the known ways, with impregnation with an aqueous solution of a suitable water-soluble, decomposable compound being preferred.

An optional ingredient for the activated multimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith—for example, an embodiment wherein the hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type and either prior to or after the ruthenium carbonyl reagent is added thereto; however, best results are ordinarily obtained when the metallic halide is sublimed onto the surface of the carrier material after the ruthenium carbonyl is added thereto according to the preferred method disclosed in U.S. Pat. No. 2,999,074. The component can generally be utilized in any amount which is catalytically effective, with a value selected from the range of about 1 to about 100 wt. % of the carrier material generally being preferred.

According to the present invention, a hydrocarbon charge stock and hydrogen are contacted with the instant activated multimetallic catalyst in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use either a fixed bed system or a dense-phase moving bed system such as is shown in U.S. Pat. No. 3,725,249. It is also contemplated that the contacting step can be performed in the presence of a physical mixture of particles of the catalyst of the present invention and particles of a conventional dual-function catalyst of the prior art. In a fixed bed system, a hydrogen-rich gas and the charge stock are preheated by any suitable heating means to the desired reaction temperature and then are passed into a conversion zone containing a fixed bed of the selectively sulfided acidic multimetallic catalyst. It is, of course, understood that the conversion zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase.

In the case where the activated multimetallic catalyst of the present invention is used in a reforming operation, the reforming system will typically comprise a reforming zone containing one or more fixed beds or dense-phase moving beds of the catalysts. In a multiple bed system, it is, of course, within the scope of the present invention to use the present catalyst in less than all of the beds with a conventional dual-function catalyst being used in the remainder of the beds. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines, partially reformed gasolines, and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° F. to about 150° F. and an end boiling point within the range of from about 325° F. to about 425° F., or may be a selected fraction thereof which generally will be a higher boiling fraction commonly referred to as a heavy naphtha—for example, a naphtha boiling in the range of $C_7$ to 400° F. In some cases, it is also advantageous to charge pure hydrocarbons or mixtures of hydrocarbons that have been extracted from hydrocarbon distillates—for example, straightchain paraffins—which are to be converted to aromatics. It is preferred that these charge stocks be treated by conventional catalytic pretreatment methods such as hydrorefining, hydrotreating, hydrodesulfurization, etc. to remove substantially all sulfurous, nitrogenous, and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment, the charge stock can be a paraffinic stock rich in $C_4$ to $C_8$ normal paraffins, or a normal butane-rich stock, or an n-hexane-rich stock, or a mixture of xylene isomers, or an olefin-containing stock, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromatic, a naphthene, and the like. In hydrocracking embodiments, the charge stock will be typically a gas oil, heavy cracked cycle oil, etc. In addition, alkylaromatics, olefins, and naphthenes can be conveniently isomerized by using the catalyst of the present invention. Likewise, pure hydrocarbons or substantially pure hydrocarbons can be converted to more valuable products by using the acidic multimetallic catalyst of the present invention in any of the hydrocarbon conversion processes, known to the art, that use a dual-function catalyst.

In a reforming embodiment, it is generally preferred to utilize the activated multimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 50 ppm., preferably less than 20 ppm. and most preferably less than 10 ppm., expressed as weight of equivalent water in the charge stock. In general, this can be accomplished by careful control of the water present in the charge stock and in the hydrogen stream. The charge stock can be dried by using any suitable drying means known to the art, such as a conventional solid adsorbent having a high selectivity for water, for instance, sodium or calcium crystalline aluminosilicates, silica gel, activated alumina, molecular sieves, anhydrous calcium sulfate, high surface area sodium, and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. In an especially preferred mode of operation, the charge stock is dried to a level corresponding to less than 5 wt. ppm. of water equivalent. In general, it is preferred to maintain the hydrogen stream entering the hydrocarbon conversion zone at a level of about 10 vol. ppm. of water or less and most preferably about 5 vol. ppm. or less. If the water level in the hydrogen stream is too high, drying of same can be conveniently accomplished by contacting the hydrogen stream with a suitable desiccant such as those mentioned above.

In the reforming embodiment, an effluent stream is withdrawn from the reforming zone and passed through a cooling means to a separation zone, typically maintained at about 25° F. to 150° F., wherein a hydrogen-rich gas stream is separated from a high octane liquid product stream, commonly called as unstabilized reformate. When the water level in the hydrogen stream is outside the range previously specified, at least a portion of this hydrogen-rich gas stream is withdrawn from the separating zone and passed through an adsorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling front-end volatility of the resulting reformate.

The operating conditions utilized in the numerous hydrocarbon conversion embodiments of the present invention are in general those customarily used in the art for the particular reaction, or combination of reactions, that is to be effected. For instance, alkylaromatic, olefin, and paraffin isomerization conditions include: a temperature of about 32° F. to about 1000° F. and preferably from about 75° F. to about 600° F., a pressure of atmospheric to about 100 atmospheres, a hydrogen to hydrocarbon mole ratio of about 0.5:1 to about 20:1, and an LHSV (calculated on the basis of equivalent liquid volume of the charge stock contacted with the catalyst per hour divided by the volume of conversion zone containing catalyst and expressed in units of hr.$^{-1}$) of about 0.2 to 10. Dehydrogenation conditions include: a temperature of about 700° F. to about 1250° F., a pressure of about 0.1 to about 10 atmospheres, a liquid hourly space velocity of about 1 to 40, and a hydrogen to hydrocarbon mole ratio of about 1:1 to 20:1. Likewise, typical hydrocracking conditions include: a pressure of about 500 psig. to about 3000 psig., a temperature of about 400° F. to about 900° F., an LHSV of about 0.1 to about 10, and hydrogen circulation rates of about 1000 to 10,000 SCF per barrel of charge.

In the reforming embodiment of the present invention, the pressure utilized is selected from the range of about 0 psig. to about 1000 psig., with the preferred pressure being about 50 psig. to about 600 psig. Particularly good results are obtained at low or moderate pressure; namely, a pressure of about 100 to 450 psig. In fact, it is a singular advantage of the present invention that it allows stable operation at lower pressures than have heretofore been successfully utilized in so-called "continuous" reforming systems (i.e. reforming for periods of about 15 to about 200 or more barrels of charge per pound of catalyst without regeneration) with conventional platinum-ruthenium catalyst systems. In other words, the activated multimetallic catalyst of the present invention allowed the operation of a continuous reforming system to be conducted at lower pressure (i.e. 100 to about 350 psig.) for about the same or better catalyst cycle life before regeneration as has been heretofore realized with conventional platinum-ruthenium catalysts at higher pressure (i.e. 300 to 600 psig.). On the other hand, the extraordinary activity and activity-stability characteristics of the catalyst of the present invention relative to a conventional platinum-ruthenium catalyst enables reforming operations conducted at pressures of 300 to 600 psig. to achieve substantially increased catalyst cycle life before regeneration.

The average temperature required for reforming with the instant catalyst is markedly lower than that required for a similar reforming operation using a conventional platinum-ruthenium or platinum-rhenium catalyst of the prior art. This significant and desirable feature of the present invention is a consequence of the superior average activity of the activated multimetallic catalyst of the present invention for the octane-upgrading reactions that are preferably induced in a typical reforming operation. Hence, the present invention requires a temperature in the range of from about 775° F. to about 1100° F. and preferably about 850° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Therefore, it is a feature of the present invention that not only is the initial temperature requirement lower, but also the rate at which the temperature is increased in order to maintain a constant octane product is substantially superior for the instant catalyst system than for an equivalent operation with a high quality platinum-ruthenium or platinum-rhenium catalyst system of the prior art. Moreover, for the catalyst of the present invention, the average $C_5+$ yield and the $C_5+$ yield stability are substantially better than for a platinum-ruthenium reforming catalyst of the prior art. The superior activity, selectivity and stability characteristics of the instant catalyst can be utilized in a number of highly beneficial ways to enable increased performance of a catalytic reforming process relative to that obtained in a similar operation with a platinum-ruthenium or platinum-rhenium catalyst of the prior art, some of these are: (1) Octane number of $C_5+$ product can be increased without sacrificing average $C_5+$ yield and/or catalyst run length. (2) The duration of the process operation (i.e. catalyst run length or cycle life) before regeneration becomes necessary can be increased. (3) $C_5+$ yield can be further increased by lowering average reactor pressure with no change in catalyst run length. (4) Investment costs can be lowered without any sacrifice in cycle life or in $C_5+$ yield by lowering recycle gas requirements thereby saving on capital cost for compressor capacity or by lowering initial catalyst loading requirements thereby saving on cost of catalyst and on capital cost of the reactors. (5) Throughput can be increased significantly at no sacrifice in catalyst cycle life or in $C_5+$ yield if sufficient heater capacity is available.

The reforming embodiment of the present invention also typically utilizes sufficient hydrogen to provide an amount of about 1 to about 20 moles of hydrogen per mole of hydrocarbon entering the reforming zone, with excellent results being obtained when about 2 to about 6 moles of hydrogen are used per mole of hydrocarbon. Likewise, the liquid hourly space velocity (LHSV) used in reforming is selected from the range of about 0.1 to about 10, with a value in the range of about 1 to about 5 being preferred. In fact, it is a feature of the present invention that it allows operations to be conducted at higher LHSV than normally can be stably achieved in a continuous reforming process with a high quality platinum-ruthenium reforming catalyst of the prior art. This last feature is of immense economic significance because it allows a continuous reforming process to operate at the same throughput level with less catalyst inventory or at greatly increased throughput level with the same catalyst inventory than that heretofore used with conventional platinum-ruthenium reforming catalyst at no sacrifice in catalyst life before regeneration.

The following examples are given to illustrate further the preparation of the activated and multimetallic catalytic composite of the present invention and the use thereof in the conversion of hydrocarbons. It is understood that the examples are intended to be illustrative rather than restrictive.

EXAMPLE I

A sulfur-free alumina carrier material comprising 1/16 inch spheres was prepared by: forming an aluminum hydroxy chloride sol by dissolving substantially pure aluminum pellets in a hydrochloric acid solution, adding hexamethylenetetramine to the resulting alumina sol, gelling the resulting solution by dropping it into an oil bath to form spherical particles of an alumina hydrogel, aging and washing the resulting particles and finally drying and calcining the aged and washed particles to form spherical particles of gamma-alumina containing on an elemental basis, about 0.3 wt. % combined chlorine. Additional details as to this method of preparing the preferred gamma-alumina carrier material are given in the teachings of U.S. Pat. No. 2,620,314.

An aqueous impregnation solution containing chloroplatinic acid, perrhenic acid and hydrogen chloride was then prepared. The alumina carrier material particles were thereafter admixed with this impregnation solution. The amounts of the metallic reagents contained in this impregnation solution were calculated to result in a final composite containing, on an elemental basis, about 0.375 wt. % platinum and about 0.25 wt. % rhenium. In order to insure uniform dispersion of the platinum component throughout the carrier material, the amount of hydrogen chloride used in this impregnation solution was about 2 wt. % of the alumina particles. This impregnation step was performed by adding the carrier material particles to the impregnation mixture with constant agitation. In addition, the volume of the solution was approximately the same as the bulk volume of the alumina carrier material particles so that all of the particles were immersed in the impregnation solution. The impregnation mixture was maintained in contact with the carrier material particles for a period of about $\frac{1}{2}$ to about 3 hours at a temperature of about 70° F. Thereafter, the temperature of the impregnation mixture was raised to about 225° F. and the excess solution was evaporated in a period of about 1 hour. The resulting dried impregnated particles were then subjected to an oxidation treatment in a dry air stream at a temperature of about 975° F. and a GHSV of about 500 hr.$^{-1}$ for about $\frac{1}{2}$ hour. This oxidation step was designed to convert substantially all of the platinum ingredient to the corresponding platinum oxide form. The resulting oxidized spheres were subsequently contacted in a halogen treating step with an air stream containing $H_2O$ and HCl in a mole ratio of about 30:1 for about 2 hours at 975° F. and a GHSV of about 500 hr.$^{-1}$ in order to adjust the halogen content of the catalyst particles to a value of about 1 wt. %. The halogen-treated spheres were thereafter subjected to a second oxidation step with a dry air stream at 975° F. and a GHSV of 500 hr.$^{-1}$ for an additional period of about $\frac{1}{2}$ hour.

The resulting oxidized, halogen-treated, platinum- and rhenium-containing carrier material particles were then subjected to a dry reduction treatment designed to reduce substantially all of the platinum component to the elemental state and to maintain a uniform dispersion of this component in the carrier material. This reduction step was accomplished by contacting the particles with a hydrocarbon-free, dry hydrogen stream containing less than 5 vol. ppm. $H_2O$ at a temperature of about 1050° F., a pressure slightly above atmospheric, a flow rate of hydrogen through the particles corresponding to a GHSV of about 400 hr.$^{-1}$ and for a period of about one hour.

Ruthenium carbonyl complex, $Ru_3(CO)_{12}$, was thereafter dissolved in an anhydrous acetone solvent in order to prepare the ruthenium carbonyl solution which was used as the vehicle for reacting ruthenium carbonyl with the carrier material containing the uniformly dispersed platinum and rhenium. The amount of this complex used was selected to result in a finished catalyst containing about 0.1 wt. % ruthenium derived from ruthenium carbonyl. The resulting ruthenium carbonyl-containing solution was then contacted under appropriate impregnation conditions with the reduced platinum- and rhenium-containing alumina carrier material resulting from the previously described reduction step. The impregnation conditions utilized were: a contact time of about one half to about three hours, a temperature of about 70° F. and a pressure of about atmospheric. It is important to note that this impregnation step was conducted under a nitrogen blanket so that oxygen was excluded from the environment and also this step was performed under anhydrous conditions. Thereafter the acetone solvent was removed under flowing nitrogen at a temperature of about 175° F. for a period of about one hour. The resulting dry ruthenium carbonyl impregnated particles were then subjected to a pyrolysis step designed to decompose the ruthenium carbonyl components. This step involved subjecting the ruthenium carbonyl impregnated particles to a flowing hydrogen stream at a first temperature of about 230° F. for about one half hour at a GHSV of about 600 hr.$^{-1}$ and at atmospheric pressure. Thereafter in the second portion of the pyrolysis step the temperature of the impregnated particles was raised to about 575° F. for an additional interval of about one hour until the evolution of CO was no longer evident.

The resulting pyrolyzed catalytic composite was then maintained under a nitrogen blanket and cooled to a temperature of about 70° F. These catalyst particles were then loaded under a nitrogen blanket into a mild agitation device designed to slowly roll the catalyst particles so as to provide good contact between these particles and their gaseous environment. The agitation device was fitted with an inlet means designed to allow fixed quantities of $H_2S$ to be periodically injected into the gaseous environment contained therein. Initially this gaseous environment was of course pure nitrogen. The amount of $H_2S$ necessary to sulfide the catalyst to a level of about 600 wt. ppm. was then calculated. The necessary amount of $H_2S$ was then divided into five portions which were then separately added via the inlet means to the agitation device at 15 minute intervals. The conditions utilized during this sulfiding step were: a temperature of about 70° F., a pressure of about atmospheric and a contact time of sulfiding agent with the catalyst particles of about 1 and $\frac{1}{4}$ hours. The resulting sulfided catalyst was then maintained under a nitrogen blanket until it was loaded into the reactor in the subsequently described reforming test.

A sample of the resulting catalytic composite contained on an elemental basis, about 0.375 wt. % platinum, about 0.1 wt. % ruthenium derived from the carbonyl, about 0.25 wt. % rhenium, about 1.0 wt. % chlorine, and about 0.06 wt. % sulfur. The resulting catalyst is hereinafter referred to as Catalyst A. For this catalyst the atomic ratio of rhenium to platinum was about 0.7:1 and the atomic ratio of ruthenium to platinum was about 0.5:1.

EXAMPLE II

In order to compare the activated acidic multimetallic catalytic composite of the present invention with a platinum-rhenium catalyst system of the prior art in a manner calculated to bring out the beneficial interaction of the pyrolyzed ruthenium carbonyl component with the platinum and rhenium components, a comparison test was made between the catalyst of the present invention prepared in accordance with Example I, Catalyst A, and a control catalyst, Catalyst C, which was a conventional sulfided bimetallic platinum-rhenium reforming catalyst. This control catalyst was a conventional combination of platinum, rhenium, chlorine and sulfur with an alumina carrier material which was prepared by coimpregnation of platinum and rhenium using an impregnation solution containing the required amounts of chloroplatinic acid, perrhenic acid and hydrochloric acid to result in catalyst containing about 0.375 wt. % platinum, about 0.375 wt. % rhenium, about 1.0 wt. % chlorine and about 0.07 wt. % sulfur.

These catalysts were then separately subjected to a high stress accelerated catalytic reforming evaluation test designed to determine in a relatively short period of time their relative activity, selectivity, and stability characteristics in a process for reforming a relatively low-octane gasoline fraction. In all tests the same charge stock was utilized and its pertinent characteristics are set forth in Table I.

This accelerated reforming test was specifically designed to determine in a very short period of time whether the catalyst being evaluated has superior characteristics for use in a high severity reforming operation.

TABLE I

| Analysis of Charge Stock | |
|---|---|
| Gravity, API at 60° F. | 58.7 |
| Distillation Profile, °F. | |
| Initial Boiling Point | 200 |
| 5% Boiling Point | 216 |
| 10% Boiling Point | 222 |
| 30% Boiling Point | 246 |
| 50% Boiling Point | 266 |
| 70% Boiling Point | 298 |
| 90% Boiling Point | 330 |
| 95% Boiling Point | 344 |
| End Boiling Point | 364 |
| Chloride, wt. ppm. | 0.2 |
| Nitrogen, wt. ppm. | 0.1 |
| Sulfur, wt. ppm. | 0.1 |
| Water, wt. ppm. | 4 |
| Octane Number, F-1 clear | 30.2 |
| Paraffins, vol. % | 69 |
| Naphthenes, vol. % | 22 |
| Aromatics, vol. % | 9 |

Each run consisted of a series of evaluation periods of 24 hours, each of these periods comprises a 12-hour line-out period followed by a 12-hour test period during which the $C_5+$ product reformate from the plant was collected and analyzed. The test runs for the Catalysts A and C were performed at identical conditions which comprises a LHSV of 2.0 hr.$^{-1}$, a pressure of 300 psig., a 3:1 gas to oil ratio, and an inlet reactor temperature which was continuously adjusted throughout the test in order to achieve and maintain a $C_5+$ target research octane of 100.

All tests runs were performed in a pilot plant scale reforming unit comprising a reactor containing a fixed bed of the catalyst undergoing evaluation, a hydrogen separation zone, a debutanizer column, and suitable heating means, pumping means, condensing means, compressing means, and the like conventional equipment. The flow scheme utilized in this plant involves commingling a hydrogen recycle stream with the charge stock and heating the resulting mixture to the desired conversion temperature. The heated mixture is then passed downflow into a reactor containing the catalyst undergoing evaluation as a stationary bed. An effluent stream is then withdrawn from the bottom of the reactor, cooled to about 55° F. and passed to a gas-liquid separation zone wherein a hydrogen-rich gaseous phase separates from a liquid hydrocarbon phase. A portion of the gaseous phase is then continuously passed through a high surface area sodium scrubber and the resulting substantially water-free and sulfur-free hydrogen-containing gas stream is returned to the reactor in order to supply the hydrogen recycle stream. The excess gaseous phase from the separation zone is recovered as the hydrogen-containing product stream (commonly called "excess recycle gas"). The liquid phase from the separation zone is withdrawn therefrom and passed to a debutanizer column wherein light ends (i.e. $C_1$ to $C_4$) are taken overhead as debutanizer gas and $C_5+$ reformate stream recovered as the principal bottom product.

Figure 2:
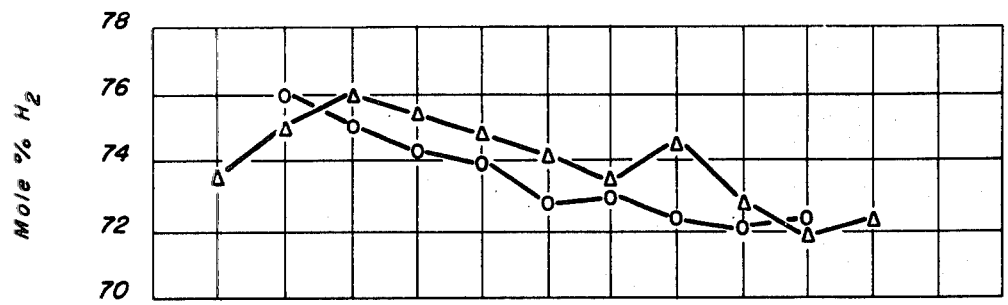
Figure 3:
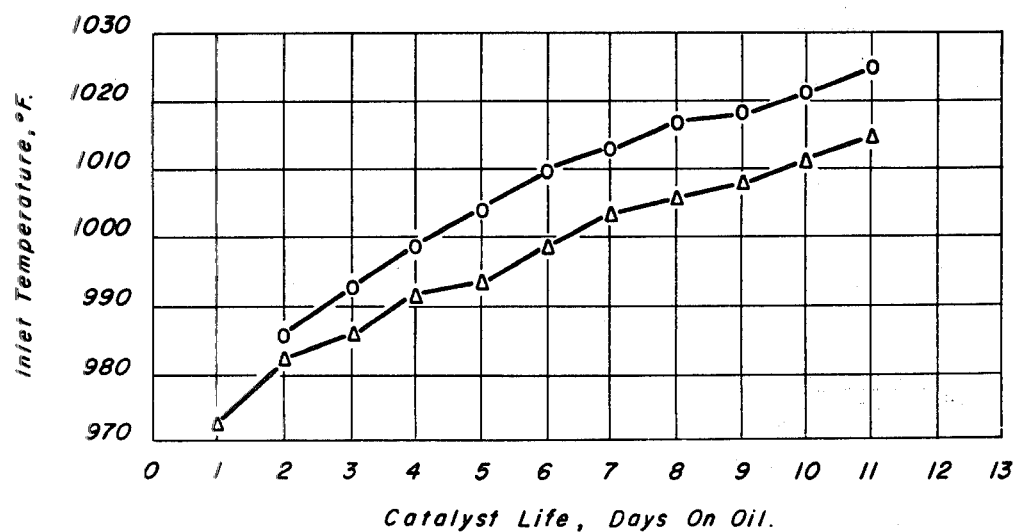

The results of the separate tests performed on the activated and attenuated catalyst of the present invention, Catalysts A, and the control catalyst of the present invention, Catalysts A, and the control catalyst, Catalysts C, are presented in FIGS. 1, 2 and 3 as a relationship between $C_5+$ yields expressed as liquid volume percent (LV%) of the charge for each of the catalysts. FIG. 2 on the other hand plots the observed hydrogen purity in mole percent of the recycle gas stream for each of the catalysts. And finally, FIG. 3 tracks inlet reactor temperature necessary for each catalyst to achieve a target research octane number of 100.

Referring now to the results of the comparison test presented in FIGS. 1, 2 and 3 for Catalysts A and C, it is immediately evident that the activated multimetallic catalytic composite of the present invention substantially outperformed the conventional platinum-rhenium control catalyst in the areas of average activity required to make octane, activity-stability and hydrogen production, without sacrificing any $C_5+$ yield or $C_5+$ yield stability. Turning to FIG. 1 it can be ascertained that the average $C_5+$ selectivity for Catalyst A was clearly equivalent to that exhibited for Catalyst C with similar yield stability. Hydrogen selectivities for these catalysts are given in FIG. 2 and it is clear from the data that there is an increase in hydrogen selectivity that accompanies the advance of the present invention. The data presented in FIG. 3 immediately highlights the surprising and significant difference in activity between the three catalyst systems. From the data presented in FIG. 3 it is clear that Catalyst A was significantly more active than the control catalyst and it is equally clear that the activity-stability of Catalyst A over the test was clearly superior to that exhibited by the control catalyst. Thus it is immediately apparent from the data in FIG. 3 that a significant and unexpected improvement in average activity characteristics is a principal advantage of the platinum-ruthenium-rhenium catalyst of the present invention. In sum, the cumulative effect of the data plotted in FIGS. 1, 2 and 3 indicate that the catalyst system of the present invention is significantly more active and stable than the control catalyst, that this increase in activity and stability is coupled with an advance in average hydrogen purity and that $C_5+$ yield is essentially the same for both catalyst systems.

In final analysis, it is clear from the data presented in FIGS. 1, 2 and 3 for Catalysts A and C that the use of a pyrolyzed ruthenium carbonyl component to interact with a platinum- and rhenium-containing catalytic composite provides an efficient and effective means for significantly promoting an acidic hydrocarbon conversion catalyst containing a platinum group metal when it is utilized in a high severity reforming operation. It is likewise clear from these results that the catalyst system of the present invention is a difference in kind rather than degree from the platinum-ruthenium and platinum-rhenium catalyst systems of the prior art.

It is intended to cover by the following claims all changes and modifications of the above disclosure of the present invention which would be self-evident to a man of ordinary skill in the hydrocarbon conversion art or in the catalyst formulation art.

I claim as my invention:

1. A catalytic composite comprising the pyrolyzed reaction product of a catalytically effective amount of a ruthenium carbonyl component with a porous carrier material containing a uniform dispersion of catalytically effective amounts of a platinum group component, which is maintained in the elemental metallic state during the incorporation and pyrolysis of the ruthenium carbonyl component, and of a rhenium component.

2. A catalytic composite as defined in claim 1 wherein the platinum group component is platinum.

3. A catalytic composite as defined in claim 1 wherein the platinum group component is palladium.

4. A catalytic composite as defined in claim 1 wherein the platinum group component is rhodium.

5. A catalytic composite as defined in claim 1 wherein the platinum group component is iridium.

6. A catalytic composite as defined in claim 1 wherein the platinum group component is ruthenium.

7. A catalytic composite as defined in claim 1 wherein the porous carrier material contains a catalytically effective amount of a halogen component.

8. A catalytic composite as defined in claim 7 wherein the halogen component is combined chlorine.

9. A catalytic composite as defined in claim 1 wherein the porous carrier material is a refractory inorganic oxide.

10. A catalytic composite as defined in claim 9 wherein the refractory inorganic oxide is alumina.

11. A catalytic composite as defined in claim 1 wherein the composite contains the components in amounts, calculated on an elemental metallic basis, corresponding to about 0.01 to about 2 wt. % platinum group metal, about 0.01 to about 5 wt. % rhenium, and about 0.01 to about 2 wt. % ruthenium, derived from the ruthenium carbonyl component.

12. A catalytic composite as defined in claim 7 wherein the halogen component is present therein in an amount sufficient to result in the composite containing, on an elemental basis, about 0.1 to about 3.5 wt. % halogen.

13. A catalytic composite as defined in claim 1 wherein the metals content thereof is adjusted so that the atomic ratio of rhenium to the platinum group metal is about 0.1:1 to about 10:1 and the atomic ratio of ruthenium, derived from the ruthenium carbonyl component, to the platinum group metal is about 0.1:1 to about 5:1.

14. A catalytic composite as defined in claim 7 wherein the composite contains, on an elemental basis, about 0.05 to about 1 wt. % platinum group metal, about 0.05 to about 1 wt. % ruthenium, derived from the ruthenium carbonyl component, about 0.05 to about 1 wt. % rhenium and about 0.5 to about 1.5 wt. % halogen.

15. A catalytic composite as defined in claim 1 wherein the composite is prepared by the steps of: (a) reacting a ruthenium carbonyl complex with a porous carrier material containing a uniform dispersion of the platinum group component maintained in the elemental metallic state and of the rhenium component, and thereafter, (b) subjecting the reaction product from step (a) to pyrolysis conditions selected to decompose the resulting ruthenium carbonyl component.

16. A catalytic composite as defined in claim 15 wherein the pyrolysis step is conducted under anhydrous conditions and in the substantial absence of free oxygen.

* * * * *